(12) United States Patent
Rachwal et al.

(10) Patent No.: US 6,177,569 B1
(45) Date of Patent: Jan. 23, 2001

(54) OXO-PYRIDOIMIDAZOLE-CARBOXAMIDES: GABA BRAIN RECEPTOR LIGANDS

(75) Inventors: Bogumila Rachwal, Branford; Pamela Albaugh; Kenneth Shaw, both of Clinton, all of CT (US)

(73) Assignee: Neurogen Corporation, Branford, CT (US)

( * ) Notice: Under 35 U.S.C. 154(b), the term of this patent shall be extended for 0 days.

(21) Appl. No.: 09/383,297

(22) Filed: Aug. 25, 1999

Related U.S. Application Data

(60) Provisional application No. 60/097,841, filed on Aug. 25, 1998.

(51) Int. Cl.⁷ .................. C07D 471/12; C07D 498/00
(52) U.S. Cl. .................. 546/86; 64/194; 544/126; 544/361
(58) Field of Search .................. 546/86, 64, 194; 544/126, 361

(56) References Cited

U.S. PATENT DOCUMENTS

| | | | |
|---|---|---|---|
| 5,639,760 | 6/1997 | Maryanoff et al. | 546/86 |
| 5,817,668 | 10/1998 | Reitz et al. | 514/292 |

FOREIGN PATENT DOCUMENTS

| | | |
|---|---|---|
| WO 94/04532 | 3/1994 | (WO) . |
| WO 98/15553 | 4/1998 | (WO) . |

OTHER PUBLICATIONS

Maryanoff, Bruce, et al., "Potential Anxiolytic Agents. 2. Improvement of Oral Efficacy for the Pyridol [1,2-a] Benzimidazole (PBI) Class of GABA–A Receptor Modulators" *Bioorg. Med. Chem. Lett.* 1996, 6 (3), 333,338.

Maryanoff, Bruce, et al., Potential Axiolytic Agents Pyrido [1,2-a] benzimidazoles: A New Structural Class of Ligands for the Benzodiazepine Binding Site on GABA-A Receptors, *J. Med. Chem.* 1995, 38 (1), 16–20.

Maryanoff B. E. et al., "Potential Anxiolytic Agents. 3. Novel A–ring Modified Pyrido '1,2–azimidazoles", Bioorganic & Medicinal Chemistry Letters, GB, Oxford, vol. 9, No. 11, Jun. 7, 1999, pp. 1547–1552.

J.H. Cohen et al., "Pocess Research for the Synthesis of RWJ–51204, A Novel Anxiolytic Agent", Chemical Abstracts, Vol. 131, No. 13, 1999, p. 806.

J.H. Cohen et al., "Process Research for the Synthesis of RWJ–51204, A Novel Anxiolytic Agent", Organic Process Research & Development, vol. 3, No. 4, 1999, pp. 260–265.

*Primary Examiner*—Amelia Owens
(74) *Attorney, Agent, or Firm*—McDonnell Boehnen Hulbert & Berghoff; Steven J. Sarussi

(57) ABSTRACT

Disclosed are compounds of the formula:

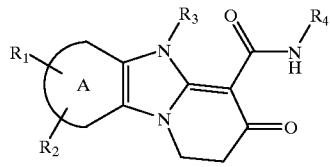

or the pharmaceutically acceptable non-toxic salts thereof where $R_1$–$R_4$ and A are defined herein, which compounds are highly selective agonists, antagonists or inverse agonists for GABAa brain receptors or prodrugs of agonists, antagonists or inverse agonists for GABAa brain receptors and are, therefore, useful in the diagnosis and treatment of anxiety, Down Syndrome, depression, sleep, cognitive and seizure disorders, overdose with benzodiazepine drugs and for enhancement of alertness.

57 Claims, No Drawings

OXO-PYRIDOIMIDAZOLE-CARBOXAMIDES: GABA BRAIN RECEPTOR LIGANDS

This is a continuation-in-part of application Ser. No. 60/097,841, filed Aug. 25, 1998.

BACKGROUND OF THE INVENTION

1. Field of the Invention

This invention relates to novel oxo-pyridoimidazole-carboxamides which selectively bind to GABAa receptors. This invention also relates to pharmaceutical compositions comprising such compounds and to the use of such compounds in enhancing alertness and treating anxiety, overdoses of benzodiazepine-type drugs, Down Syndrome, depression and sleep, seizure and cognitive disorders. The interaction of certain substituted oxo-pyridoimidazole-carboxamides of the invention with a GABA binding site, the benzodiazepine (BDZ) receptor, is described. This interaction results in the pharmacological activities of these compounds.

2. Description of the Related Art

γ-Aminobutyric acid GABA) is regarded as one of the major inhibitory amino acid transmitters in the mammalian brain. Over 40 years have elapsed since its presence in the brain was demonstrated (Roberts & Frankel, J. Biol. Chem. 187: 55–63, 1950; Udenfriend, J. Biol. Chem. 187: 65–69, 1950). Since that time, an enormous of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Drugs that interact at the GABAa receptor can possess a spectrum of pharmacological activities depending on their abilities to modify the action of GABA.

The 1,4-Benzodiazepines, such as diazepam, continue to be among the most widely used drugs in the world as anxiolytics, sedative-hypnotics, muscle relaxants, and anti-convulsants. A number of these compounds are extremely potent drugs; such potency indicates a site of action with a high affinity and specificity for individual receptors. Early electrophysiological studies indicated that a major action of benzodiazepines was enhancement of GABAergic inhibition. Recently, those compounds possessing activity similar to the benzodiazepines are called agonists. Compounds possessing activity opposite to benzodiazepines are called inverse agonists, and the compounds blocking both types of activity have been termed antagonists.

The GABAa receptor subunits have been cloned from bovine and human cDNA libraries (Schoenfield et al., 1988; Duman et al., 1988). A number of distinct cDNAs were identified as subunits of the GABAa receptor complex by cloning and expression. These are categorized into α,β,γ,δ,ε, and provide a molecular basis for the GABAa receptor heterogeneity and distinctive regional pharmacology (Shivvers et al., 1980; Levitan et al., 1989). The γ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior. Depending on the mode of interaction, these compounds are capable of producing a spectrum of activities (either sedative, anxiolytic, and anticonvulsant, or wakefulness, seizures, and anxiety).

U.S. Pat. No. 5,639,760, PCT publication WO 94/04532, Bioorg. Med. Chem. Lett. 1996, 6 (3), 333–338, and J. Med. Chem. 1995, 38 (1), 16–20 disclose 3-oxo-pyrido[1,2-a]-benzimidazole-4-carboxyl and 4-oxo-azepino[1,2-a]-benzimidazole-5-carboxyl derivatives, useful as muscle relaxants, hypnotics/sedatives, anxiolytics, anticonvulsants/antiepileptics, anti-inebriants, and antidotes for benzodiazepine overdose.

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in the diagnosis and treatment of anxiety, Down Syndrome, depression, sleep, cognitive and seizure disorders, overdose with benzodiazepine drugs and for enhancement of alertness. Accordingly, a broad embodiment of the invention is directed to compounds of Formula I:

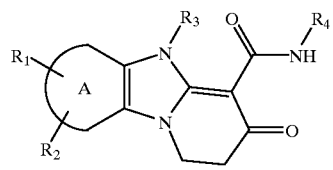

wherein:

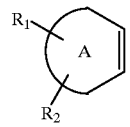

represents a carbocyclic-containing ring system which is optionally substituted with up to two groups $R_1$ and $R_2$;

$R_1$ and $R_2$ are the same or different and represent halogen, $C_1$–$C_6$ alkyl, $C_1$–$C_6$ alkoxy, $C_3$–$C_7$ cycloalkyl, $C_3$–$C_7$ cycloalkoxy, each of which may be optionally substituted with $NR_5R_6$;

$R_5$ and $R_6$ are the same or different and represent hydrogen, $C_1$–$C_6$ alkyl, $C_3$–$C_7$ cycloalkyl; or $R_5$ and $R_6$ may be taken together to form a nitrogen containing ring having from 5–7 members;

$R_3$ represents hydrogen, $C_1$–$C_6$ alkyl, $C_1$–$C_6$ alkoxy ($C_1$–$C_6$)alkyl, $C_3$–$C_7$ cycloalkyl, or $C_3$–$C_7$ cycloalkoxy $C_1$–$C_6$ alkyl, $C_3$–$C_7$ cycloalkyl, where any $R_3$ with the exception of hydrogen may be substituted with $NR_5R_6$; and $R_4$ is aryl, heteroaryl, arylalkyl, or heteroarylalkyl, where each aryl group is optionally substituted with up to three groups independently selected from halogen, hydroxy, $C_1$–$C_6$ alkyl, $C_3$–$C_7$ cycloalkyl, mono- or di($C_1$–$C_6$)alkylamino, or $C_1$–$C_6$ alkoxy or $C_3$–$C_7$ cycloalkoxy, either of which may be substituted with $NR_5R_6$;

provided that (i) if $R_3$ is not substituted with $NR_5R_6$, then either $R_1$ or $R_4$ is substituted with $NR_5R_6$;

(ii) if $R_4$ is not substituted with $NR_5R_6$, then either $R_1$ or $R_3$ is substituted with $NR_5R_6$;

(iii) if $R_1$ is not substituted with $NR_5R_6$, then either $R_2$ or $R_4$ is substituted with $NR_5R_6$; and (iv) if $R_3$ is substituted with $NR_5R_6$, $R_4$ is arylalkyl or heteroarylalkyl, where each aryl group is optionally substituted with up to three groups independently selected from halogen, hydroxy, $C_1$–$C_6$ alkyl, $C_3$–$C_7$ cycloalkyl, mono- or di($C_1$–$C_6$)alkylamino, or $C_1$–$C_6$ alkoxy or $C_3$–$C_7$ cycloalkoxy, either of which may be substituted with $NR_5R_6$.

These compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, Down Syndrome, depression, sleep, cognitive and seizure disorders, overdose with benzodiazepine drugs and for enhancement of alertness.

DETAILED DESCRIPTION OF THE INVENTION

The novel compounds encompassed by the invention can be described by the general Formula I set forth above or the pharmaceutically acceptable non-toxic salts The invention provides compounds with Formula II that are within the scope of Formula I:

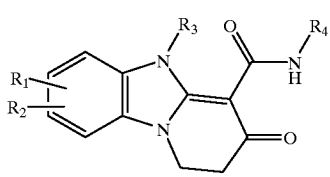

II wherein:

$R_1$, $R_2$, $R_3$, and $R_4$ are as defined above.

In addition, the invention provides compounds of Formula III:

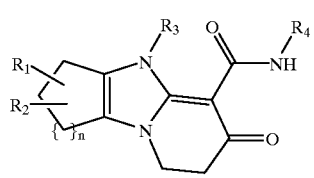

III where $R_1$, $R_2$, $R_3$, and $R_4$ are as defined above and n is 1, 2, or 3.

The present invention also encompasses compounds of Formula IV:

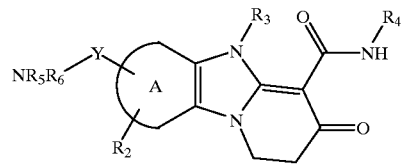

wherein $R_2$, $R_3$, $R_4$, $R_5$, and $R_6$ are as defined above, and Y is $C_1$–$C_6$ alkyl, $C_1$–$C_6$ alkoxy, $C_3$–$C_7$ cycloalkyl, or $C_3$–$C_7$ cycloalkoxy.

In addition, the invention provides compounds of Formula V:

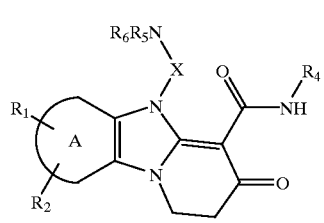

V wherein $R_1$, $R_2$, $R_5$, and $R_6$ are as defined above and $R_4$ is arylalkyl or heteroarylalkyl, where each aryl group is optionally substituted with up to three groups independently selected from halogen, hydroxy, $C_1$–$C_6$ alkyl, $C_3$–$C_7$ cycloalkyl, mono- or di($C_1$–$C_6$) alkylamino, or $C_1$–$C_6$ alkoxy or $C_3$–$C_7$ cycloalkoxy, either of which may be substituted with $NR_5R_6$; and X is $C_1$–$C_6$ alkyl, $C_1$–$C_6$ alkoxy, $C_1$–$C_6$ alkyl($C_1$–$C_6$) alkoxy, $C_3$–$C_7$ cycloalkyl, or $C_3$–$C_7$ cycloalkoxy.

Further, the invention provides compounds of Formula VI:

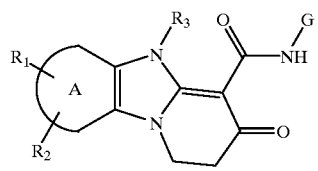

$R_1$, $R_2$, and $R_3$ are as defined above and G represents:

(i) a group of the formula

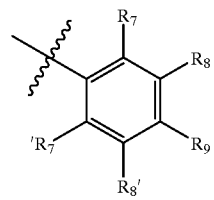

where $R_7$, $R_{7'}$, $R_8$, $R_{8'}$, and $R_9$ are the same or different and are selected from hydrogen, halogen, hydroxy, $C_1$–$C_6$ alkyl, $C_3$–$C_7$ cycloalkyl, —$OR_{10}$, or —$NR_{11}R_{12}$; or $R_8$ and $R_9$ taken together with the atoms to which they are attached form a (hetero) cyclic ring wherein $R_{10}$ is $C_1$–$C_6$ alkyl or $C_3$–$C_7$ cycloalkyl; and $R_{11}$ and $R_{12}$ are the same or different and represent hydrogen, $C_1$–$C_6$ alkyl, $C_3$–$C_7$ cycloalkyl, or $R_{11}$ and $R_{12}$ together with the nitrogen to which they are attached form a 3–7 membered ring;

(ii) a group of the formula:

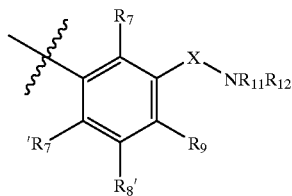

where X, $R_7$, $R_{7'}$, $R_8$, $R_{8'}$, $R_9$, and $NR_{11}R_{12}$ are as defined above;

(iii) a group of the formula:

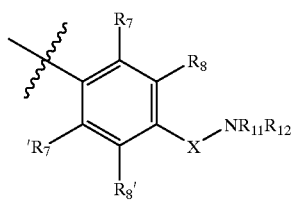

where X, $R_7$, $R_{7'}$, $R_8$, $R_{8'}$, and $NR_{11}R_{12}$ are as defined above;

(iv) a group of the formula:

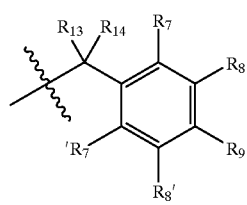

where $R_7$, $R_{7'}$, $R_8$, $R_{8'}$, and $R_9$ are as defined above and $R_{13}$ and $R_{14}$ independently represent hydrogen, $C_1$–$C_6$ alkyl, $C_3$–$C_7$ cycloalkyl, or $R_{13}$ and $R_{14}$ taken together with the carbon atom to which they are attached form $C_3$–$C_7$ cycloalkyl;

(v) a group of the formula:

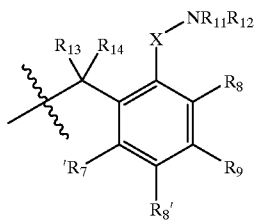

where X, $R_7$, $R_8$, $R_{8'}$, $R_9$, $R_{13}$, $R_{14}$ and $NR_{11}R_{12}$ are as defined above;

(vi) a group of the formula:

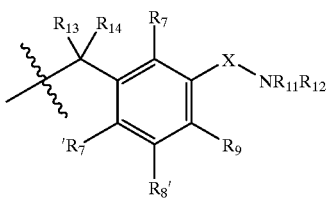

where X, $R_7$, $R_{7'}$, $R_{8'}$, $R_9$, $R_{13}$, $R_{14}$ and $NR_{11}R_{12}$ are as defined above;

(vii) a group of the formula:

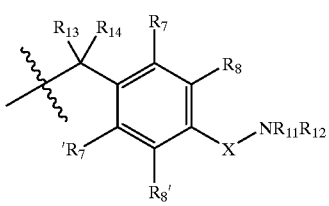

where X, $R_7$, $R_{7'}$, $R_8$, $R_{8'}$, $R_{13}$, $R_{14}$ and $NR_{11}R_{12}$ are as defined above;

(viii) a group of the formula:

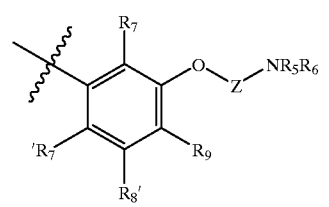

where $R_7$, $R_{7'}$, $R_{8'}$, $R_9$, and $NR_5R_6$ are as defined above and

Z is $C_2$–$C_6$ alkylene or $C_2$–$C_6$ alkyleneoxy($C_2$–$C_6$) alkyl, or Z may be taken together with $R_5$ or $R_6$ to form a heterocyclic ring;

(ix) a group of the formula:

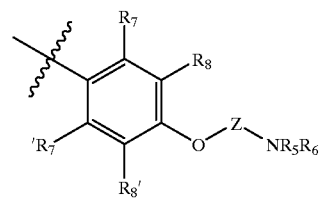

where Z, $R_7$, $R_{7'}$, $R_8$, $R_{8'}$, and $NR_5R_6$ are as defined above;

(x) a group of the formula:

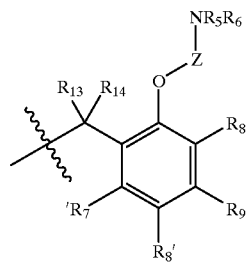

where Z, $R_{7'}$, $R_8$, $R_{8'}$, $R_9$, $R_{13}$, $R_{14}$ and $NR_5R_6$ are as defined above;

(xi) a group of the formula:

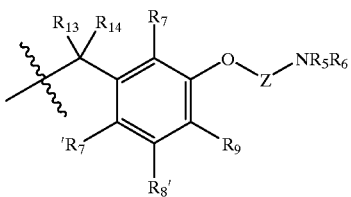

where Z, $R_7$, $R_{7'}$, $R_{8'}$, $R_9$, $R_{13}$, $R_{14}$, and $NR_5R_6$ are as defined above;

(xii) a group of the formula:

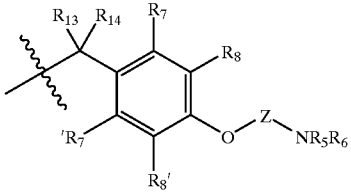

where Z, $R_7$, $R_{7'}$, $R_8$, $R_{8'}$, $R_{13}$, $R_{14}$, and $NR_5R_6$ are as defined above;

(xiii) a group of the formula:

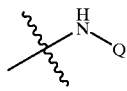

where Q represents a heteroaryl group;

(xiv) a group of the formula:

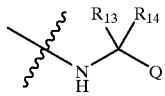

where $R_{13}$, $R_{14}$ and Q are as defined above;

(xv) a group of the formula:

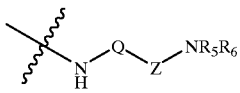

where Z, Q, and $NR_5R_6$ are as defined above;

(xiv) a group of the formula:

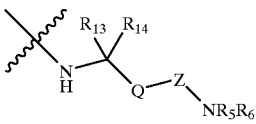

where Z, Q, $R_{13}$, $R_{14}$, and $NR_5R_6$ are as defined above.

Preferred compounds of the invention include those of Formula 1A:

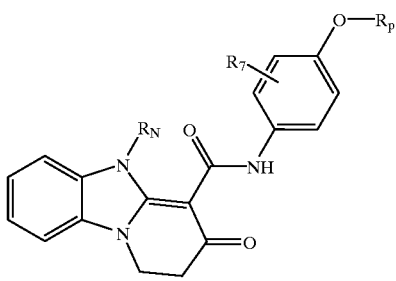

1A where $R_7$ represents hydrogen, halogen preferably chloro or fluoro, hydroxy or methyl;

$R_N$ represents hydrogen, $C_1$–$C_2$ alkyl, $C_1$–$C_2$ alkoxy ($C_1$–$C_2$)alkyl or $R_aR_bN(C_1$–$C_3)$alkyl where $R_a$ and $R_b$ independently represent hydrogen or $C_1$–$C_6$ alkyl or $R_aR_bN$ represents a $C_3$–$C_7$ nitrogen-containing ring which ring is optionally substituted with a nitrogen or oxygen atom and which ring may optionally be further substituted with $C_1$–$C_6$ alkyl; and $R_p$ represents $R_aR_bN(C_1$–$C_4)$alkyl or $R_aR_bN(C_1$–$C_4)$alkoxy($C_1$–$C_4$)alkyl where each $R_a$ and $R_b$ independently represents hydrogen or $C_1$–$C_6$ alkyl or $R_aR_bN$ represents a $C_3$–$C_7$ nitrogen-containing ring which ring is optionally substituted with a nitrogen or oxygen atom and which ring may optionally be further substituted with $C_1$–$C_6$ alkyl; or $R_p$ represents a group of the formula:

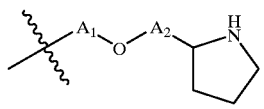

where each of $A_1$ and $A_2$ is independently $C_1$–$C_4$, preferably $C_2$–$C_3$ alkylene.

Particularly preferred compounds of Formula 1A are those where $R_7$ is hydrogen or fluoro; $R_N$ is ethyl, hydrogen, methyl, ethoxyethyl, 2-piperidinylethyl, ethylaminoethyl or methylaminoethyl; and $R_p$ is

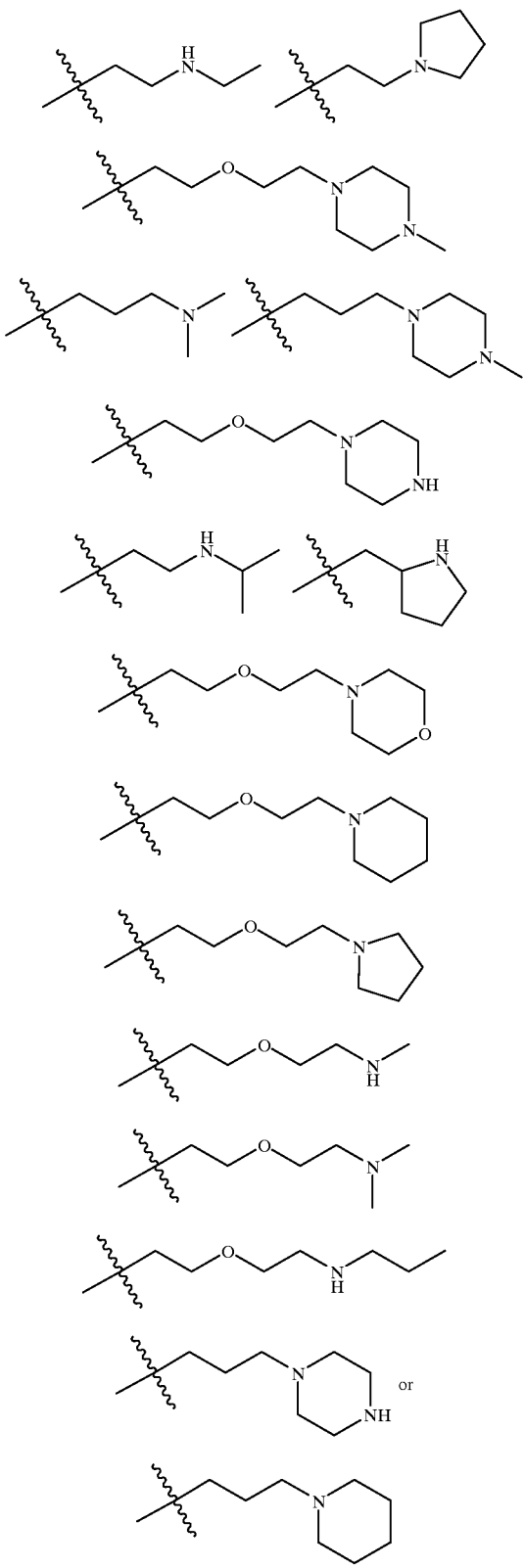

Other preferred compounds of the invention include those of Formula 1B:

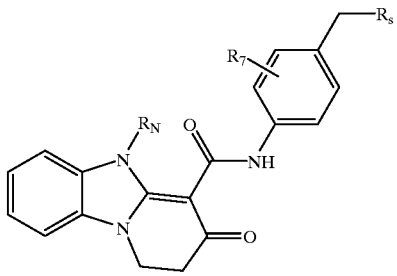

where
R$_7$ represents hydrogen, halogen preferably chloro or fluoro, hydroxy or methyl;

R$_N$ represents hydrogen, C$_1$–C$_2$ alkyl, C$_1$–C$_2$ alkoxy (C$_1$–C$_2$)alkyl or R$_a$R$_b$N(C$_1$–C$_3$)alkyl where R$_a$ and R$_b$ independently represent hydrogen or C$_1$–C$_6$ alkyl or R$_a$R$_b$N represents a C$_3$–C$_7$ nitrogen-containing ring which ring is optionally substituted with a nitrogen or oxygen atom and which ring may optionally be further substituted with C$_1$–C$_6$ alkyl; and R$_s$ represents R$_a$R$_b$N(C$_1$–C$_4$)alkyl where each R$_a$ and R$_b$ independently represents hydrogen or C$_1$–C$_6$ alkyl or R$_a$R$_b$N represents a C$_3$–C$_7$ nitrogen-containing ring which ring is optionally substituted with a nitrogen or oxygen atom and which ring may optionally be further substituted with C$_1$–C$_6$ alkyl.

By a C$_3$–C$_7$ nitrogen-containing ring (R$_a$R$_b$N represents a C$_3$–C$_7$ nitrogen-containing ring) that is optionally substituted with a nitrogen atom and further substituted with C$_1$–C$_6$ alkyl, is meant rings such as 4-methylpiperazinyl or 4-methylimidazolidinyl.

In certain situations, compounds of Formula I may contain one or more asymmetric carbon atoms, so that the compounds can exist in different stereoisomeric forms. These compounds can be, for example, racemates or optically active forms. In these situations, the single enantiomers, i. e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid and base addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitic, bencoic, citric, tartaric, maleic, hydroiodic, alkanoic such as acetic, HOOC—(CH$_2$)n—ACOOH where n is 0–4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

The present invention also encompasses the acylated prodrugs of the compounds of Formula I. Those skilled in the are will recognize various synthetic methodologies which may be employed to prepare non-toxic pharmaceutically acceptable addition salts and acylated prodrugs of the compounds encompassed by Formula I.

By lower alkyl in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By cycloalkyl in the present invention is meant cycloalkyl groups having 3–7 atoms such as, for example cyclopropyl, cyclobutyl, cyclopenyl, cyclohexyl, and cycloheptyl.

By aryl in the present invention is meant an aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl).

By arylalkyl in the present invention is meant an alkyl group moiety substituted with an aryl group. By heteroarylalkyl in the present invention is meant an alkyl group moiety substituted with an heteroaryl group.

By lower alkoxy in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, and 3-methylpentoxy.

By halogen in the present invention is meant fluorine, bromine, chlorine, and iodine.

By heteroaryl (aromatic heterocycle) in the present invention is meant one or more aromatic ring systems of 5-, 6-, or 7-membered rings containing at least one and up to four hetero atoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, naphthyridinyl, benzimidazolyl, and benzoxazolyl.

Specific examples of heteroaryl groups are the following:

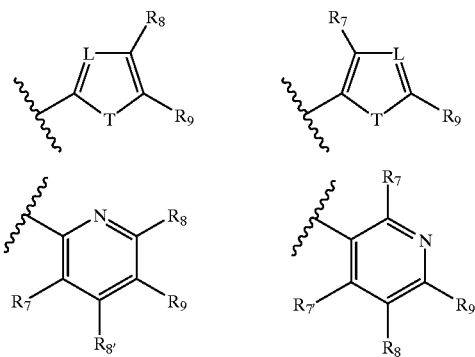

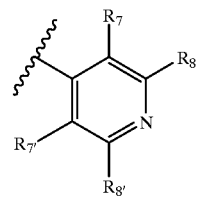

-continued wherein

L is nitrogen or —$CR_{15}$;

T is —$NR_{15}$, oxygen, or sulfur;

$R_7$, $R_8$, $R_9$, $R_{7'}$, and $R_{8'}$ are as defined above; and $R_{15}$ is hydrogen, lower alkyl having 1–6 carbon atoms, or lower cycloalkyl having 3–7 carbon atoms.

The definition of Formula I as shown in the specification and as used in the claims includes possible isomers, such as tautomers and rotamers. The Formulae Ic and Id illustrate this point.

For Formula I, when R=H:

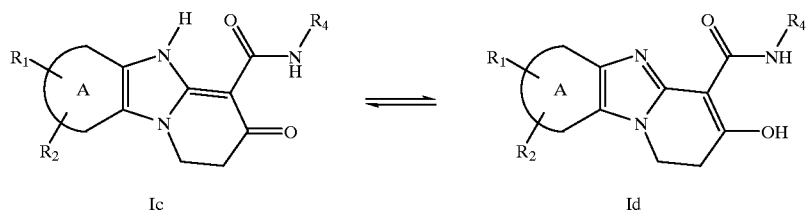

Ic          Id

Representative compounds of the invention are shown below in Table 1.

TABLE 1

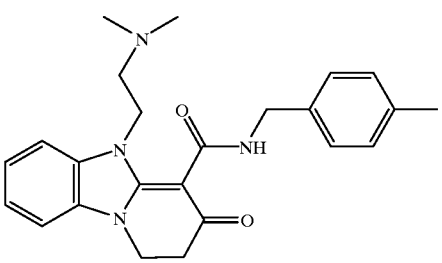

1

TABLE 1-continued

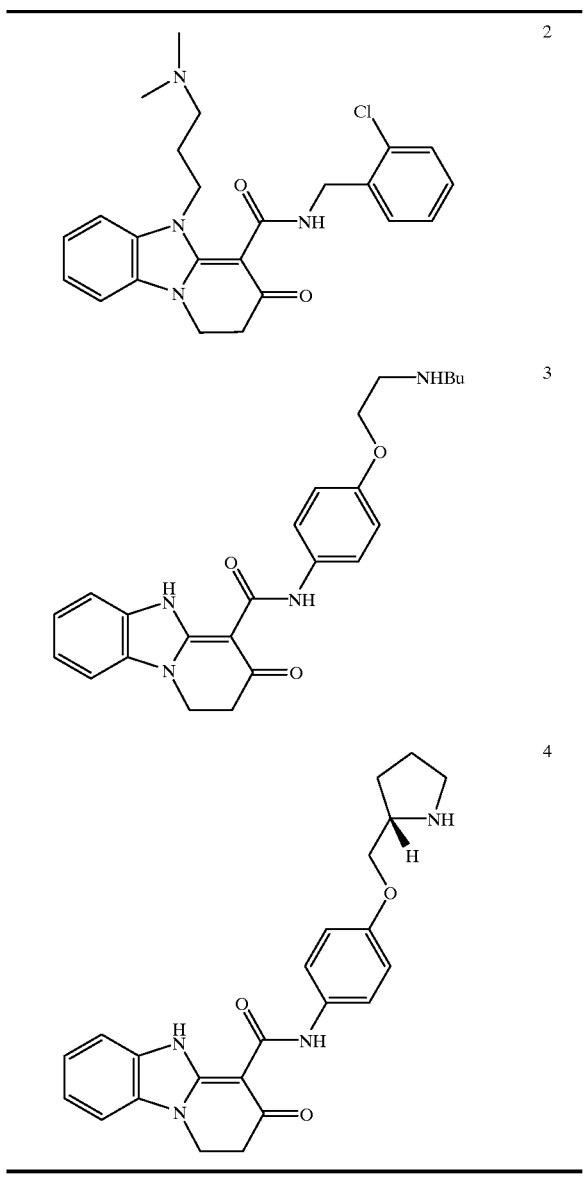

The compounds of Formula I and their salts are suitable for the diagnosis and treatment of anxiety, Down Syndrome, sleep, cognitive and seizure disorders, and overdose with benzodiazepine drugs and for enhancement of alertness, both in human and non-human animals and domestic pets, especially dogs and cats and farm animals such as sheep, swine and cattle.

The dipyridoimidazole-oxo-carboxamides of Formula I and their salts are suitable for the diagnosis and treatment of anxiety, Down Syndrome, depression, sleep, cognitive and seizure disorders, and overdose with benzodiazepine drugs and for enhancement of alertness, both in human and non-human animals and domestic pets, especially dogs and cats and farm animals such as sheep, swine and cattle.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It will be convenient to formulate these animal feed and drinking water compositions with a mullet-dose of the drug so that the animal takes in an appropriate quantity of the composition along with its diet. It will also be convenient to present the composition as a premix for addition to the feed or drinking water.

An illustration of the preparation of compounds of the present invention is given in Scheme 1.

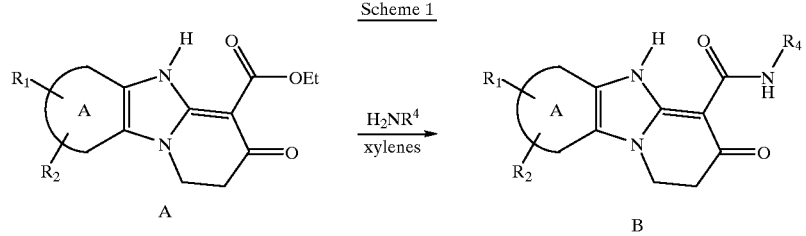

Scheme 1

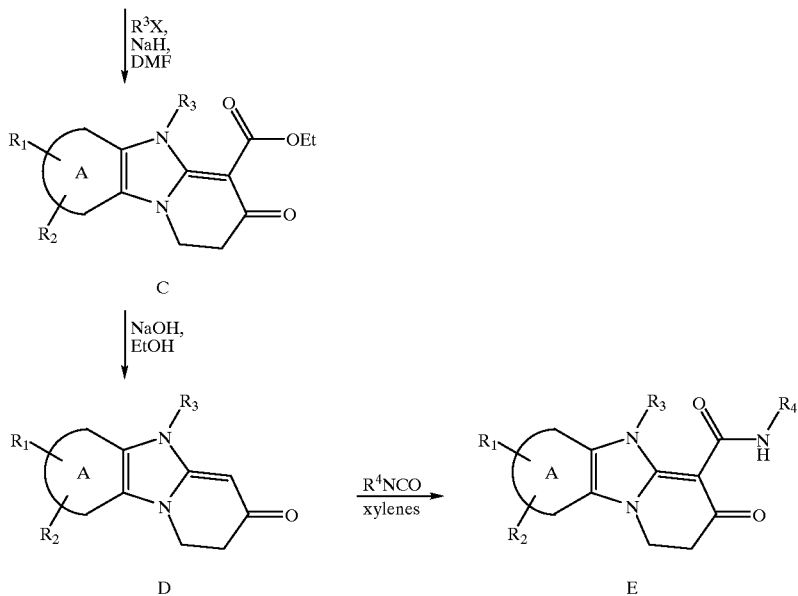

In Scheme 1, the substituents $R_1$, $R_2$, $R_3$, and $R_4$ carry the definitions set forth above for Formula I.

Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, the need for such protecting groups will be apparant to those skilled in the art of organic synthesis as well as the conditions necessary to attach and remove such groups.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic and/or inorganic sources, or prepared using well known synthetic methods.

Representative examples of methods for preparing intermediates of the invention are set forth below.

EXAMPLE 1

Ethyl 1,2-dihydro-3-hydroxy-pyrido[1,2-a]benzimidazole-4-carboxylate is prepared according to literature procedure (Marynoff et al, J. Med. Chem., 1995, 38, 16–20; Marynoff, McComsey, and Winston, WO 94/04532).

EXAMPLE 2

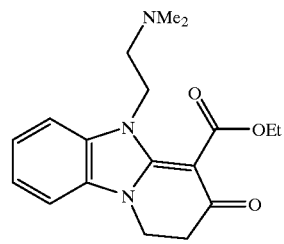

1.)

2-Dimethylaminoethylchloride hydrochloride is stirred with 10 M aqueous NaOH (4 mL) and ether (20 mL) for one hour. The ether layer is decanted and the aqueous layer is washed with ether (10 ml). The combined ether layers are dried over $Na_2SO_4$, decanted, and treated with molecular sieves overnight. To a suspension of ethyl 1,2-dihydro-3-hydroxy-pyrido[1,2-a]benzimidazole-4-carboxylate (1.3 g 5 mmol) in DMF (25 mL) is added in one portion the ethereal solution. The reaction mixture is stirred for 15 min, then a suspension of sodium hydride (0.6 g, 15 mmol, 60% in oil) in DMF (5 mL) is added in one portion. After stirring at ambient temperature for 15 min, the mixture is heated at 110° C. for 2 h. The mixture is cooled, concentrated, and water is added (20 mL). The resulting mixture is extracted 2X with chloroform (100 mL). The combined organic layers are dried and concentrated to afford ethyl 5-(2-dimethylaminoethyl)-3-oxo-1,2,3,5-tetrahydropyrido [1,2-a]benzimidazole-4-carboxylate.

2.)

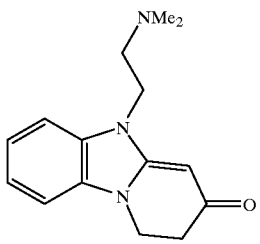

A solution of ethyl 5-(2-dimethylaminoethyl)-3-oxo-1, 2,3,5-tetrahydropyrido[1,2-a]benzimidazole-4-carboxylate (1.0 g, 3 mmol) in ethanol (40 mL) and 10 M aqueous NaOH (20 ml) is heated at reflux for 2 h. The reaction mixture is cooled and the layers separated. The upper layer is diluted with ether (100 mL), washed with water (20 mL), dried, and concentrated to yield 5-(2-dimethylaminoethyl)-3-oxo-1,2, 3,5-tetrahydropyrido [1,2-a]benzimidazole.

3.)

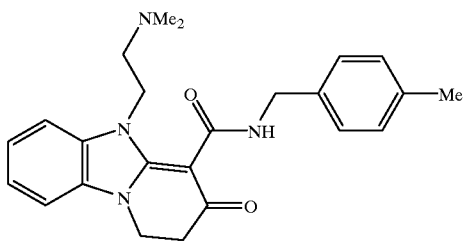

A mixture of p-tolylisocyanate (74 mg, 0.5 mmol) and 5-(2-dimethylaminoethyl)-3-oxo-1, 2,3,5-tetrahydropyrido [1,2-a ]benzimidazole (100 mg, 0.4 mmol) in chloroform (2 mL) is heated at reflux for 2 h. The mixture is cooled, concentrated, and the residue purified on silica gel to give N-(4 -Methylbenzyl)-5-(2-dimethylaminoethyl)-3-oxo-1,2, 3,5-tetrahydropyrido [1,2-a]benzimidazole-4-carboxamide; m.p. 120–122° C. (Compound 1).

EXAMPLE 3

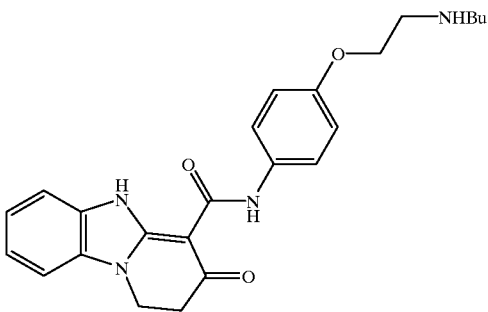

4-(2-N-t-Butoxcarbonyl-n-butylaminoethoxy)aniline (62 mg, 0.2 mmol) and ethyl 1,2-dihydro-3-hydroxy-pyrido[1, 2-a ]benzimidazole-4-carboxylate (52 mg, 0.2 mmol) in xylenes (2 mL) are heated at 130–140° C. for 2 h. The solvent is evaporated and the residue triturated with ether. The resulting solid is treated with methanol (2 mL) and 1 M HCl in ether (2 mL) at ambient temperature for 1 h. The solvent is evaporated and the residue triturated with ether to give N-[4-(2-butylaminoethoxy) phenyl]-1,2-dihydro-3-hydroxy-pyrido[1,2-a ]benzimidazole-4-carboxamide hydrochloride; m.p. 70–85° C. (Compound 3).

EXAMPLE 4

The following compounds were prepared essentially according to the procedures described in Examples 1–3:
a) N-(4-Methoxybenzyl)-5-(2-dimethylaminoethyl)-3-oxo-1, 2,3,5-tetrahydropyrido[1,2-a]benzimidazole-4-carboxamide); m.p. 95–97° C. (Compound 6).
b) N-(2-Chlorobenzyl)-5-(2-dimethylaminoethyl)-3-oxo-1, 2,3, 5-tetrahydropyrido[1,2-a]benzimidazole-4-carboxamide; m.p. 138–140° C. (Compound 7).
c) N-Benzyl-5-(2-dimethylaminoethyl)-3-oxo-1,2,3,5-tetrahydropyrido [1,2-a]benzimidazole-4-carboxamide (Compound 8).
d) N-[1-(1-Napthyl)ethyl]-5-(2-dimethylaminoethyl)-3-oxo-1, 2,3,5-tetrahydropyrido[1,2-a]benzimidazole-4-carboxamide (Compound 9).
e) N-(2-Chlorobenzyl)-5-(3-dimethylaminopropyl)-3-oxo-1, 2,3,5-tetrahydropyrido[1,2-a]benzimidazole-4-carboxamide (Compound 2).
f) N-[4-(2-Ethylaminoethoxy)phenyl]-1,2-dihydro-3-hydroxy-pyrido [1,2-a]benzimidazole-4-carboxamide hydrochloride; m.p. 60–65° C. (Compound 10).
g) N-[3-(2-Diethylaminoethoxy)phenyl]-1,2-dihydro-3-hydroxy-pyrido [1,2-a]benzimidazole-4-carboxamide (Compound 11).
h) N-[4-(2-Cyclopropylaminoethoxy)phenyl]-1,2-dihydro-3-hydroxy-pyrido [1,2-a]benzimidazole-4-carboxamide hydrochloride (Compound 12).
i) N-[3-(2-Isopropylaminoethoxy)phenyl]-1,2-dihydro-3-hydroxy-pyrido [1,2-a]benzimidazole-4-carboxamide (Compound 13).
j) N-[4-(3-Butylaminopropoxy)phenyl]-1,2-dihydro-3-hydroxy-pyrido [1,2-a]benzimidazole-4-carboxamide hydrochloride.
k) N-[3-(2-Propylaminoethoxy)phenyl]-1,2-dihydro-3-hydroxy-pyrido [1,2-a]benzimidazole-4-carboxamide hydrochloride (Compound 15).
l) N-(R)-[4-(Pyrrolidinomethoxy)phenyl)-1,2-dihydro-3-hydroxy-pyrido [1,2-a]benzimidazole-4-carboxamide hydrochloride; m.p. 130–142° C. (Compound 5).
m) N-(S)-[4-(Pyrrolidinomethoxy)phenyl]-1,2-dihydro-3-hydroxy-pyrido [1,2-a]benzimidazole-4-carboxamide hydrochloride; m.p. 130–142° C. (Compound 4).
n) N-[4-(2-Pyrrolidinoethoxy)phenyl]-1,2-dihydro-3-hydroxy-pyrido [1,2-a]benzimidazole-4-carboxamide hydrochloride; m.p. 130–142° C. (Compound 16).
o) N-[4-(2-Diethylaminoethoxy)pyrid-3-yl]-1,2-dihydro-3-hydroxy-pyrido [1,2-a]benzimidazole-4-carboxamide hydrochloride; m.p. 175–178° C. (Compound 17).
p) N-[4-(2-Pyrrolidinoethoxy)pyrid-3-yl]-1,2-dihydro-3-hydroxy-pyrido [1,2-a]benzimidazole-4-carboxamide hydrochloride; m.p. 170–174° C. (Compound 18).
q) N-[4-(2-Piperidinoethoxy)pyrid-3-yl]-1,2-dihydro-3-hydroxy-pyrido [1,2-a]benzimidazole-4-carboxamide; m.p. 225–230° C. (Compound 19).
r) N-[4-(t-Butylaminoethoxy)pyrid-3-yl]-1,2-dihydro-3-hydroxy-pyrido [1,2-a)benzimidazole-4-carboxamide hydrochloride (Compound 20).
s) N-[4-(2-Ethylaminoethoxy)pyrid-3-yl]-1,2-dihydro-3-hydroxy-pyrido [1,2-a]benzimdazole-4-carboxamide hydrochloride (Compound 21).

t) N-{4-[2-(2-Pyrrolidinoethoxy)ethoxy]pyrid-3-yl}-1,2-dihydro-3-hydroxy-pyrido[1,2-a]benzimidazole-4-carboxamide hydrochloride; m.p. 55–65° C. (Compound 22).

u) N-[4-(3-Pyrrolidinopropoxy)pyrid-3-yl]-1,2-dihydro-3-hydroxy-pyrido [1,2-a]benzimidazole-4-carboxamide hydrochloride; m.p. 60–68° C. (Compound 23).

v) N-(4-methylbenzyl)-5-(3-dimethylaminopropyl)-3-oxo-1, 2,3,5-tetrahydropyrido[1,2-a]benzimidazole-4-carboxamide (Compound 24).

w) N-benzyl-5-(3-dimethylaminopropyl)-3-oxo-1,2,3,5-tetrahydropyrido [1,2-a]benzimidazole-4-carboxamide (Compound 25).

x) N-[4-(2-Ethylaminoethoxy)phenyl]5-ethyl-3-oxo-1, 2,3,5-tetrahydropyrido[1,2-a]benzimidazole-4-carboxamide (Compound 26).

y) N-[4-(3-Piperidin-1-yl-propoxy)benzyl]5-ethyl-3-oxo-1, 2,3,5-tetrahydropyrido[1,2-a]benzimidazole-4-carboxamide (Compound 27).

z) N-[2-Fluoro-4-(3-piperidin-1-yl-propoxy)benzyl]5-ethyl-3-oxo-1,2,3,5-tetrahydropyrido[1,2-a] benzimidazole-4-carboxamide (Compound 28).

aa) N-[4-(3-Dimethylaminopropoxy)benzyl]5-ethyl-3-oxo-1, 2,3,5-tetrahydropyrido[1,2-a]benzimidazole-4-carboxamide (Compound 29).

bb) N-[2-Fluoro-4-(2-pyrrolidin-1-yl-ethoxy)benzyl]5-ethyl-3-oxo-1,2,3,5-tetrahydropyrido[1,2-a] benzimidazole-4-carboxamide (Compound 30).

cc) N-(R)-[4-(Pyrrolidin-2-yl-methoxy)phenyl]5-ethyl-3-oxo-1, 2,3,5-tetrahydropyrido [1,2-a]benzimidazole-4-carboxamide (Compound 31).

dd) N-(S)-[4-(Pyrrolidin-2-yl-methoxy)phenyl]5-ethyl-3-oxo-1, 2,3,5-tetrahydropyrido[1,2-a]benzimidazole-4-carboxamide (Compound 32).

ee) N-[4-(2-Isopropylaminoethoxy)phenyl]5-ethyl-3-oxo-1, 2,3,5-tetrahydropyrido-[1,2-a]benzimidazole-4-carboxamide (Compound 33).

ff) N-{4-[2-(2-Pyrrolidin-1-yl-ethoxy)ethoxy]phenyl}1,2-dihydro-3-hydroxy-pyrido [1,2-a]benzimidazole-4-carboxamide (Compound 34).

gg) N-(R)-[3-Fluoro-4-(pyrrolidin-2-yl-methoxy)phenyl] 1,2-dihydro-3-hydroxy-pyrido[1,2-a]benzimidazole-4-carboxamide (Compound 35).

h) N-(S)-[3-Fluoro-4-(pyrrolidin-2-yl -methoxy)phenyl] 1,2-dihydro-3-hydroxy-pyrido[1,2-a]benzimidazole-4-carboxamide (Compound 36).

ii) N-{4-[2-(2-Morpholin-4-yl-ethoxy)ethoxy]phenyl}1, 2-dihydro-3-hydroxy-pyrido [1,2-a]benzimidazole-4-carboxamide (Compound 37).

jj) N-(4-{2-[2-(4-Methylpiperazin-1-yl) ethoxy] ethoxy}phenyl)1,2-dihydro-3-hydroxy-pyrido[1,2-a]benzimidazole-4-carboxamide (Compound 38).

kk) N-(R)-[3-Fluoro-4-(pyrrolidin-2-yl-methoxy)phenyl] 5-ethyl-3-oxo-1,2,3,5-tetrahydropyrido [1,2-a] benzimidazole-4-carboxamide (Compound 39).

ll) N-(S)-[3-Fluoro-4-(Pyrrolidin-2-yl-methoxy)phenyl] 5-ethyl-3-oxo-1,2,3,5-tetrahydropyrido[1,2-a] benzimidazole-4-carboxamide (Compound 40).

mm) N-(4-{2-[2-(4-Methylpiperazin-1-yl) ethoxy] ethoxy)benzyl]1,2-dihydro-3-hydroxy-pyrido[1,2-a]benzimidazole-4-carboxamide (Compound 41)

nn) N-{4-[2-(2-Morpholin-4-yl-ethoxy)ethoxy]benzyl}1, 2-dihydro-3-hydroxy-pyrido[1,2-a]benzimidazole-4-carboxamide (Compound 42).

oo) N-(4-{2-[2-(Methylamino)ethoxy]ethoxy}benzyl) 1,2-dihydro-3-hydroxy-pyrido[1,2-a]benzimidazole-4-carboxamide (Compound 43) (Compound 27)

pp) N-(4-{2-[2-(Butylamino)ethoxy]ethoxy)benzyl]1,2-dihydro-3-hydroxy-pyrido[1,2-a]benzimidazole-4-carboxamide (Compound 44).

qq) N-(4-{2-[2-(Dimethylamino)ethoxy]ethoxy[benzyl] 1,2-dihydro-3-hydroxy-pyrido [1,2-a]benzimidazole-4-carboxamide (Compound 45)

rr) N-(2-Fluoro-{4-[3-(4-methylpiperazin-1-yl) propoxy] benzyl) 1,2-dihydro-3-hydroxy-pyrido [1,2-a]benzimidazole-4-carboxamide (Compound 46).

ss) N-{4-[(Propylamino)methyl]phenyl}1,2-dihydro-3-hydroxy-pyrido [1,2-a]benzimidazole-4-carboxamide (Compound 27).

tt) N-{4-[(4-Methylpiperazin-1-yl)methyl]phenyl}1,2-dihydro-3-hydroxy-pyrido[1,2-a]benzimidazole-4-carboxamide (Compound 47).

uu) N-{4-[2-(Ethylamino)ethoxy]phenyl}5-(2-ethoxyethyl)-3-oxo-1,2,3,5-tetrahydropyrido[1,2-a] benzimidazole-4-carboxamide (Compound 48).

vv) N-[4-(Pyrrolidin-1-yl-methyl)phenyl]1,2-dihydro-3-hydroxy-pyrido [1,2-a]benzimidazole-4-carboxamide (Compound 27).

ww) N-{4-[2-(Ethylamino)ethoxy}5-(2-piperidin-1-yl-ethyl)-3-oxo-1,2,3,5-tetrahydropyrido[1,2-a] benzimidazole-4-carboxamide (Compound 49).

xx) N-[4-(2-Piperidin-1-yl-ethoxy)benzyl]5-(2-ethoxyethyl)-3-oxo-1,2,3,5-tetrahydropyrido[1,2-a]benzimidazole-4-carboxamide (Compound 50).

yy) N-[4-(2-Piperidin-1-yl-ethoxy)benzyl]5-(2-ethylaminoethyl)-3-oxo-1,2,3,5-tetrahydropyrido[1,2-a]benzimidazole-4-carboxamide (Compound 51).

zz) N-[4-(2-Piperidin-1-yl-ethoxy)benzyl]5-ethyl-3-oxo-1, 2,3,5-tetrahydropyrido[1,2-a]benzimidazole-4-carboxamide (Compound 52).

aaa) N-(4-{2-[(2-Morpholin-4-yl-ethyl)amino] ethoxy}benzyl) 5-ethyl-3-oxo-1,2,3,5-tetrahydropyrido[1,2-a]benzimidazole-4-carboxamide (Compound 53).

bbb) N-[4-(2-Ethylaminoethoxy)phenyl]5-ethyl-3-oxo-1, 2,3,5-tetrahydropyrido[1,2-a]benzimidazole-4-carboxamide citrate (Compound 54).

ccc) N-[4-(3-Piperidin-1-yl-propoxy)benzyl]5-ethyl-3-oxo-1, 2,3,5-tetrahydropyrido[1,2-a]benzimidazole-4-carboxamide hydrochloride (Compound 55).

ddd) N-[2-Fluoro-4-(3-piperidin-1-yl-propoxy)benzyl]5-ethyl-3-oxo-1,2,3,5-tetrahydropyrido[1,2-a] benzimidazole-4-carboxamide fumarate (Compound 56).

eee) N-[4-(3-Dimethylaminopropoxy)benzyl]5-ethyl-3-oxo-1, 2,3,5-tetrahydropyrido[1,2-a]benzimidazole-4-carboxamide hydrochloride (Compound 57).

fff) N-[2-Fluoro-4-(2-pyrrolidin-1-yl-ethoxy)benzyl]5-ethyl-3-oxo-1,2,3,5-tetrahydropyrido[1,2-a] benzimidazole-4-carboxamide hydrochloride (Compound 58).

ggg) N-(R)- (4-(Pyrrolidin-2-yl-methoxy)phenyl]5-ethyl-3-oxo-1, 2,3,5-tetrahydropyrido[1,2-a)benzimidazole-4-carboxamide hydrochloride (Compound 59).

hhh) N-(S)-[4-(Pyrrolidin-2-yl-methoxy)phenyl]5-ethyl-3-oxo-1, 2,3,5-tetrahydropyrido[1,2-a]benzimidazole-4-carboxamide hydrochloride (Compound 60).

iii) N-[4-(2-Isopropylaminoethoxy)phenyl]5-ethyl-3-oxo-1, 2,3,5-tetrahydropyrido-[1,2-a]benzimidazole-4-carboxamide hydrochloride (Compound 61).

jjj) N-{4-[2-(2-Pyrrolidin-1-yl-ethoxy)ethoxy]phenyl}1,2-dihydro-3-hydroxy-pyrido[1,2-a]benzimidazole-4-carboxamide hydrochloride (Compound 62).

kkk) N-(R)-[3-Fluoro-4-(pyrrolidin-2-yl-methoxy)phenyl]1,2-dihydro-3-hydroxy-pyrido[1,2-a]benzimidazole-4-carboxamide hydrochloride (Compound 63).

lll) N-(S)-[3-Fluoro-4-(pyrrolidin-2-yl-methoxy)phenyl]1,2-dihydro-3-hydroxy-pyrido[1,2-a]benzimidazole-4-carboxamide hydrochloride (Compound 64).

mmm) N-{4-[2-(2-Morpholin-4-yl-ethoxy)ethoxy]phenyl}1,2-dihydro-3-hydroxy-pyrido[1,2-a]benzimidazole-4-carboxamide hydrochloride (Compound 65).

nnn) N-(4-{2-[2-(4-Methylpiperazin-1-lyl) ethoxy]ethoxy}phenyl)1,2-dihydro-3-hydroxy-pyrido[1,2-a]benzimidazole-4-carboxamide hydrochloride (Compound 66).

ooo) N-(R)-[3-Fluoro-4-(pyrrolidin-2-yl-methoxy)phenyl]5-ethyl-3-oxo-1,2,3,5-tetrahydropyrido [1,2-a]benzimidazole-4-carboxamide hydrochloride (Compound 67).

ppp) N-(S)-[3-Fluoro-4-(Pyrrolidin-2-yl-methoxy)phenyl]5-ethyl-3-oxo-1,2,3,5-tetrahydropyrido[1,2-a]benzimidazole-4-carboxamide hydrochloride (Compound 68).

qqq) N-(4-{2-[2-(4-Methylpiperazin-1-yl)ethoxylethoxy)benzyl]1,2-dihydro-3-hydroxy-pyrido[1,2-a ]benzimidazole-4-carboxamide hydrochloride (Compound 69).

rrr) N-{4-[2-(2-Morpholin-4-yl-ethoxy)ethoxy]benzyl}1,2-dihydro-3-hydroxy-pyrido[1,2-a]benzimidazole-4-carboxamide hydrochloride (Compound 70).

sss) N-(4-{2-[2-(Methylamino)ethoxy]ethoxy}benzyl)1,2-dihydro-3-hydroxy-pyrido[1,2-a]benzimidazole-4-carboxamide hydrochloride (Compound 71).

ttt) N-(4-{2-[2-(Butylamino)ethoxy]ethoxy)benzyl]1,2-dihydro-3-hydroxy-pyrido[1,2-a]benzimidazole-4-carboxamide hydrochloride (Compound 72).

uuu) N-(4-{2-[2-(Dimethylamino)ethoxy]ethoxy)benzyl]1,2-dihydro-3-hydroxy-pyrido [1,2-a]benzimidazole-4-carboxamide hydrochloride (Compound 73).

vvv) N-(2-Fluoro-{4-[3-(4-methylpiperazin-1-yl)propoxy]benzyl)1,2-dihydro-3-hydroxy-pyrido[1,2-a ]benzimidazole-4-carboxamide hydrochloride (Compound 74).

www) N-{4-[(Propylamino)methyl]phenyl}1,2-dihydro-3-hydroxy-pyrido [1,2-a]benzimidazole-4-carboxamide (Compound 75).

xxx) N-{4-[(4-Methylpiperazin-1-yl)methyl]phenyl}1,2-dihydro-3-hydroxy-pyrido[1,2-a]benzimidazole-4-carboxamide (Compound 76).

yyy) N-(4-[2-(Ethylamino)ethoxy]phenyl}5-(2-ethoxyethyl)-3-oxo-1,2,3,5-tetrahydropyrido[1,2-a]benzimidazole-4-carboxamide hydrochloride (Compound 77).

zzz) N-[4-(Pyrrolidin-1-yl-methyl)phenyl]1,2-dihydro-3-hydroxy-pyrido [1,2-a]benzimidazole-4-carboxamide (Compound 78).

aaaa) N-{4-[2-(Ethylamino)ethoxy}5-(2-piperidin-1-yl-ethyl)-3-oxo-1,2,3,5-tetrahydropyrido[1,2-a]benzimidazole-4-carboxamide hydrochloride (Compound 79).

bbbb) N-[4-(2-Piperidin-1-yl-ethoxy)benzyl]5-(2-ethoxyethyl)-3-oxo-1,2,3,5-tetrahydropyrido[1,2-a ]benzimidazole-4-carboxamide (Compound 80).

cccc) N-[4-(2-Piperidin-1-yl-ethoxy)benzyl]5-(2-ethylaminoethyl)-3-oxo-1,2,3,5-tetrahydropyrido[1,2-a ]benzimidazole-4-carboxamide hydrochloride (Compound 81).

dddd) N-[4-(2-Piperidin-1-yl-ethoxy)benzyl]5-ethyl-3-oxo-1, 2,3,5-tetrahydropyrido[1,2-a]benzimidazole-4-carboxamide (Compound 82).

eeee) N- (4- {2-[(2-Morpholin-4-yl-ethyl) amino]ethoxy}benzyl)5-ethyl-3-oxo-1,2,3,5-tetrahydropyrido[1,2-a]benzimidazole-4-carboxamide (Compound 83).

EXAMPLE 5

The pharmaceutical utility of compounds of this invention are indicated by the following assay for GABAa receptor activity.

Assays are carried out as described in Thomas and Tallman (J. Bio. Chem. 156: 9838–9842, J. Neurosci. 3: 433–440, 1983). Rat cortical tissue is dissected and homogenized in 25 volumes (w/v) of 0.05 M Tris HCl buffer (pH 7.4 at 4° C.). The tissue homogenate is centrifuged in the cold (40°) at 20,000 x g for 20'. The supernatant is decanted and the pellet is rehomogenized in the same volume of buffer and again centrifuged at 20,000 x g. The supernatant is decanted and the pellet is frozen at −20° C. overnight. The pellet is then thawed and rehomogenized in 25 volume (original wt/vol) of buffer and the procedure is carried out twice. The pellet is finally resuspended in 50 volumes (w/vol of 0.05 M Tris HCl buffer (pH 7.4 at 40° C.).

Incubations contain 100 ml of tissue homogenate, 100 ml of radioligand 0.5 nM ($^3$H-RO15-1788 [$^3$H-Flumazenil] specific activity 80 Ci/mmol), drug or blocker and buffer to a total volume of 500 ml. Incubations are carried for 30 min at 4° C. then are rapidly filtered through GFB filters to separate free and bound ligand. Filters are washed twice with fresh 0.05 M Tris HCl buffer (pH 7.4 at 4° C.) and counted in a liquid scintillation counter. 1.0 mM diazepam is added to some tubes to determine nonspecific binding. Data are collected in triplicate determinations, averaged and % inhibition of total specific binding is calculated. Total Specific Binding=Total −Nonspecific. In some cases, the amounts of unlabeled drugs is varied and total displacement curves of binding are carried out. Data are converted to $K_i$'s. Compounds of this invention when tested in the assay described have $K_i$'s<1 μM.

In addition, the following assay may be used to determine if the compounds of the invention are agonists, antagonists, or inverse agonists, and, therefore, their specific pharmaceutical utility. The following assay can be employed to determine specific GABAa receptor activity.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Xenopus Laevis oocytes are enzymatically isolated and injected with non-polyadenylated cRNA mixed in a ratio of 4:1:4 for human derived α, β and γ subunits, respectively. For each subunit combination, sufficient message is injected to result in current amplitudes of >10 nA when 1 μM GABA is applied.

Electrophysiological recordings are carried out using the two electrode voltage-clamp technique at a membrane holding potential of −70 mV.

Compounds are evaluated against a GABA concentration that evokes <10% of the maximal evokable GABA current. Each oocyte is exposed to increasing concentrations of compound in order to evaluate a concentration/effect relationship. Compound efficacy is expressed as a percent-change in current amplitude: 100*((Ic/I)−1), where Ic is the GABA evoked current amplitude observed in the presence of compound and I is the GABA evoked current amplitude observed in the absence of compound.

Specificity of a compound for the RO15-1788 site is determined following completion of the concentration/effect curve. After washing the oocyte sufficiently to remove previously applied compound, the oocyte is exposed to GABA+1 μM RO15-1788, followed by exposure to GABA+1 μM RO15-1788+compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and EC50 values.

To evaluate average efficacy and EC50 values, the concentration/effect data are averaged across cells and fit to the logistic equation. Average values are reported as mean ± standard error.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of the formula

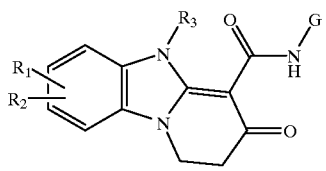

or a pharmaceutically acceptable, non-toxic salt thereof, wherein:

$R_1$ and $R_2$ are independently selected from halogen, $C_1$–$C_6$ alkyl, $C_1$–$C_6$ alkoxy, $C_3$–$C_7$ cycloalkyl, or $C_3$–$C_7$ cycloalkoxy, and where either of $R_1$ and $R_2$ may be substituted with $NR_5R_6$;

$R_5$, and $R_6$ are the same or different and represent hydrogen, $C_1$–$C_6$ alkyl, or $C_3$–$C_7$ cycloalkyl; or $R_5$ and $R_6$ and the nitrogen to which they are attached may be taken together to form a ring having from 5–7 members;

$R_3$ represents hydrogen, $C_1$–$C_6$ alkyl, $C_1$–$C_6$ alkoxy $C_1$–$C_6$ alkyl, $C_3$–$C_7$ cycloalkyl, or $C_3$–$C_7$ cycloalkoxy $C_1$–$C_6$ alkyl, where any $R_3$ with the exception of hydrogen may be substituted with $NR_5R_6$; and G represents (i) a group of the formula

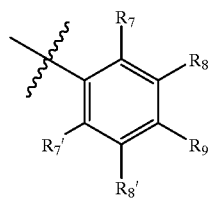

where $R_7$, $R_{7'}$, $R_8$, $R_{8'}$, and $R_9$ are the same or different and are selected from hydrogen, halogen, hydroxy, $C_1$–$C_6$ alkyl, $C_3$–$C_7$ cycloalkyl $C_1$–$C_6$ alkyl, —$OR_{10}$, or —$NR_{11}R_{12}$;

or $R_8$ and $R_9$ taken together with the atoms to which they are attached form a carbocyclic ring or a heterocyclic ring; and $R_{10}$ is $C_1$–$C_6$ alkyl or $C_3$–$C_7$ cycloalkyl, and $R_{11}$ and $R_{12}$ are the same or different and represent hydrogen, $C_1$–$C_6$ alkyl, $C_3$–$C_7$ cycloalkyl, or $R_{11}$ and $R_{12}$ together with the nitrogen to which they are attached form a 3–7 membered ring;

(ii) a group of the formula:

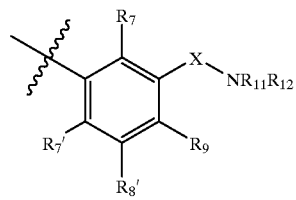

where X, $R_7$, $R_{7'}$, $R_{8'}$, $R_9$, and $NR_{11}R_{12}$ are as defined above;

(iii) a group of the formula:

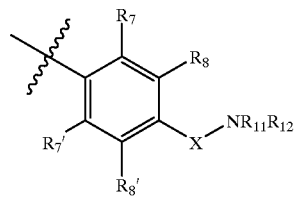

where X, $R_7$, $R_{7'}$, $R_8$, $R_{8'}$, and $NR_{11}R_2$ are as defined above;

(iv) a group of the formula:

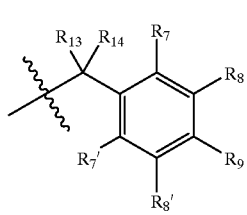

where $R_7$, $R_{7'}$, $R_8$, $R_{8'}$, and $R_9$ are as defined above and $R_{13}$ and $R_{14}$ independently represent hydrogen, $C_1$–$C_6$ alkyl, $C_3$–$C_7$ cycloalkyl, or $R_{13}$ and $R_{14}$ taken together with the carbon atom to which they are attached form a $C_3$–$C_7$ cycloalkyl;

(v) a group of the formula:

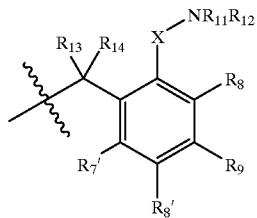

where X, $R_7$, $R_{7'}$, $R_8$, $R_{8'}$, $R_9$, $R_{13}$, $R_{14}$ and $NR_{11}R_{12}$ are as defined above;

(vi) a group of the formula:

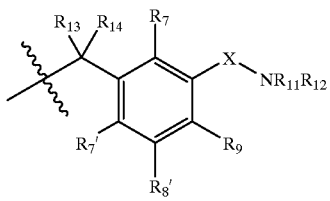

where X, $R_7$, $R_{7'}$, $R_{8'}$, $R_9$, $R_{13}$, $R_{14}$ and $NR_{11}R_{12}$ are as defined above;

(vii) a group of the formula:

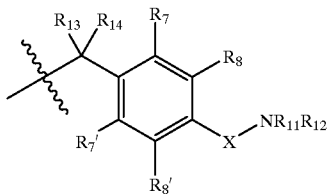

where X, $R_7$, $R_{7'}$, $R_8$, $R_{8'}$, $R_{13}$, $R_{14}$ and $NR_{11}R_{12}$ are as defined above;

(viii) a group of the formula:

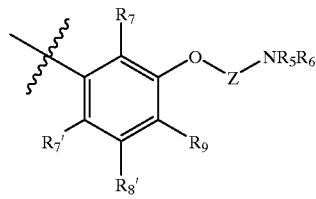

where $R_7$, $R_{7'}$, $R_{8'}$, $R_9$, and $NR_5R_6$ are as defined above and Z is $C_2$–$C_6$ alkyl, or Z may be taken together with $R_5$ or $R_6$ to form a heterocyclic ring;

(ix) a group of the formula:

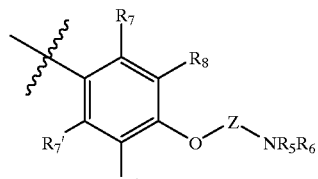

where Z, $R_7$, $R_{7'}$, $R_8$, $R_{8'}$, and $NR_5R_6$ are as defined above;

(x) a group of the formula:

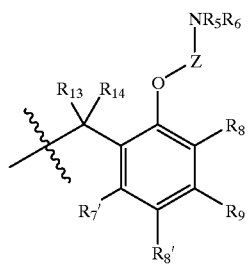

where Z, $R_{7'}$, $R_8$, $R_{8'}$, $R_9$, $R_{13}$, $R_{14}$, and $NR_5R_6$ are as defined above;

(xi) a group of the formula:

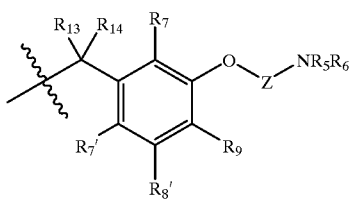

where Z, $R_7$, $R_{7'}$, $R_{8'}$, $R_9$, $R_{13}$, $R_{14}$, and $NR_5R_6$ are as defined above;

(xii) a group of the formula:

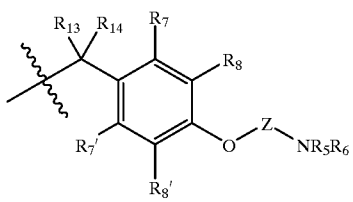

where Z, $R_7$, $R_{7'}$, $R_8$, $R_{8'}$, $R_{13}$, $R_{14}$, and $NR_5R_6$ are as defined above;

(xiii) a group of the formula:

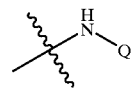

where Q represents a heteroaryl group;

(xiv) a group of the formula:

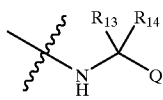

where $R_{13}$, $R_{14}$ and Q are as defined above;

(xv) a group of the formula:

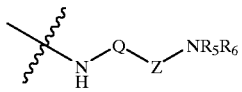

where Z, Q, and $NR_5R_6$ are as defined above; or (xvi) a group of the formula:

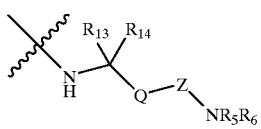

where Z, Q, $R_{13}$, $R_{14}$, and $NR_5R_6$ are as defined above.

2. A compound of the formula:

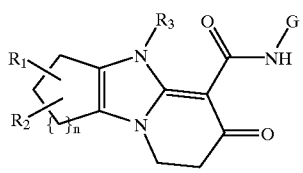

or a pharmaceutically acceptable salt thereof, wherein:
$R_1$ and $R_2$ are independently selected from halogen, $C_1$–$C_6$ alkyl, $C_1$–$C_6$ alkoxy, $C_3$–$C_7$ cycloalkyl, or $C_3$–$C_7$ cycloalkoxy, and where either of $R_1$ and $R_2$ may be substituted with $NR_5R_6$;
$R_5$ and $R_6$ are the same or different and represent hydrogen, $C_1$–$C_6$ alkyl, or $C_3$–$C_7$ cycloalkyl; or
$R_5$, $R_6$ and the nitrogen to which they are attached may be taken together to form a ring having from 5–7 members;
n is 0, 1 or 2; and
G represents
(i) a group of the formula

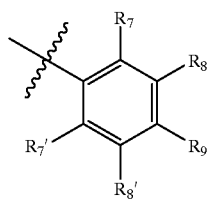

where $R_7$, $R_{7'}$, $R_8$, $R_{8'}$, and $R_9$ are the same or different and are selected from hydrogen, halogen, hydroxy, $C_1$–$C_6$ alkyl, $C_3$–$C_7$ cycloalkyl, —$OR_{10}$, or —$NR_{11}R_{22}$; or
$R_8$ and $R_9$ taken together with the atoms to which they are attached form a carbocyclic ring or heterocyclic ring; wherein $R_{10}$ is $C_1$–$C_6$ alkyl or $C_3$–$C_7$ cycloalkyl; and $R_{11}$ and $R_{12}$ are the same or different and represent hydrogen, $C_1$–$C_6$ alkyl, $C_3$–$C_7$ cycloalkyl, or $R_{11}$ and $R_{12}$ together with the nitrogen atom to which they are attached form a 3–7 membered ring;

(ii) a group of the formula:

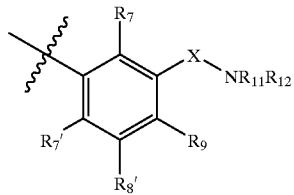

where X, $R_7$, $R_{7'}$, $R_{8'}$, $R_9$, and $NR_{11}R_{12}$ are as defined above;

(iii) a group of the formula:

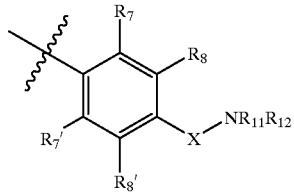

where X, $R_7$, $R_{7'}$, $R_8$, $R_{8'}$, and $NR_{11}R_{12}$ are as defined above;

(iv) a group of the formula:

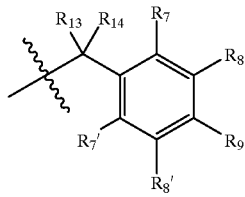

where $R_7$, $R_{7'}$, $R_8$, $R_{8'}$, and $R_9$ are as defined above; and $R_{13}$ and $R_{14}$ independently represent hydrogen, $C_1$–$C_6$ alkyl, $C_3$–$C_7$ cycloalkyl, or $R_{13}$ and $R_{14}$ taken together with the carbon atom to which they are attached form a $C_3$–$C_7$ cycloalkyl;

(v) a group of the formula:

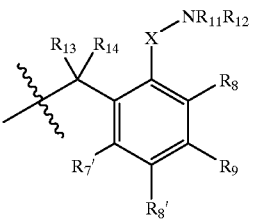

where X, $R_{7'}$, $R_8$, $R_{8'}$, $R_9$, $R_{13}$, $R_{14}$ and $NR_{11}R_{12}$ are as defined above;

(vi) a group of the formula:

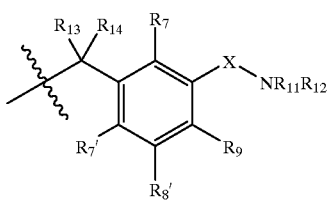

where X, $R_7$, $R_{7'}$, $R_{8'}$, $R_9$, $R_{13}$, $R_{14}$ and $NR_{11}R_{12}$ are as defined above;

(vii) a group of the formula:

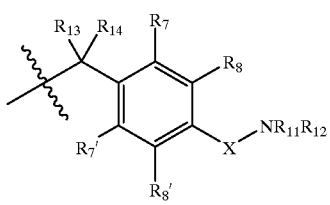

where X, $R_7$, $R_{7'}$, $R_8$, $R_{8'}$, $R_{13}$, $R_{14}$ and $NR_{11}R_{12}$ are as defined above;

(viii) a group of the formula:

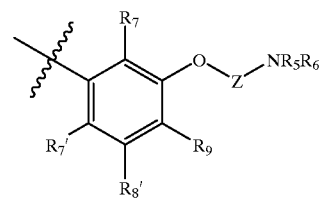

where $R_7$, $R_{7'}$, $R_{8'}$, $R_9$, and $NR_5R_6$ are as defined above and Z is $C_1$–$C_6$ alkyl, or Z may be taken together with $R_5$ or $R_6$ to form a heterocyclic ring;

(ix) a group of the formula:

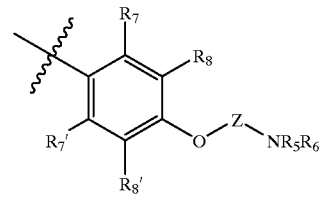

where Z, $R_7$, $R_{7'}$, $R_8$, $R_{8'}$, and $NR_5R_6$ are as defined above;

(x) a group of the formula:

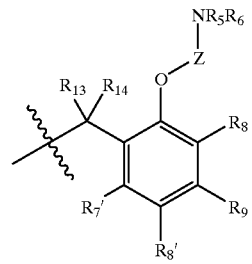

where Z, $R_7$, $R_{7'}$, $R_{8'}$, $R_9$, $R_{13}$, $R_{14}$, and $NR_5R_6$ are as defined above;

(xi) a group of the formula:

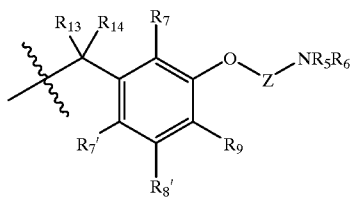

where Z, $R_7$, $R_{7'}$, $R_{8'}$, $R_9$, $R_{13}$, $R_{14}$, and $NR_5R_6$ are as defined above;

(xii) a group of the formula:

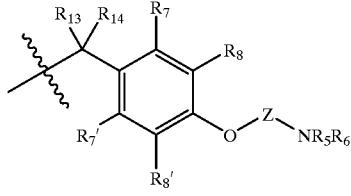

where Z, $R_7$, $R_{7'}$, $R_8$, $R_{8'}$, $R_{13}$, $R_{14}$, and $NR_5R_6$ are as defined above;

(xiii) a group of the formula:

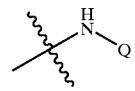

where Q represents a heteroaryl group;

(xiv) a group of the formula:

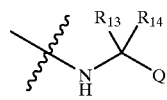

where Q, $R_{13}$ and $R_{14}$ are as defined above;

(xv) a group of the formula:

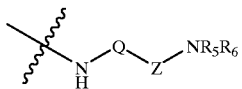

where Q, Z and NR₅R₆ are as defined above for (xv); and
(xvi) a group of the formula:

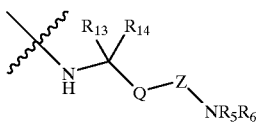

where Q, Z R₁₃, R₁₄, and NR₅R₆ are as defined above.

3. A compound according to claim 1 which is N-[4-(2-butylaminoethoxy) phenyl]1,2-dihydro-3-hydroxy-pyrido [1,2-a ]benzimidazole-4-carboxamide.

4. A compound according to claim 1 which is N-(4-methylbenzyl)-5 -(2-dimethylaminoethyl)-3-oxo-1,2,3,5-tetrahydropyrido [1,2-a]benzimidazole-4-carboxamide.

5. A compound according to claim 1 which is N-(4-methoxybenzyl)-5 -(2-dimethylaminoethyl)-3-oxo-1,2,3,5-tetrahydropyrido [1,2-a]benzimidazole-4-carboxamide).

6. A compound according to claim 1 which is N-(2-chlorobenzyl)-5 -(2-dimethylaminoethyl)-3-oxo-1,2,3,5-tetrahydropyrido [1,2-a]benzimidazole-4-carboxamide.

7. A compound according to claim 2 which is N-benzyl-5-(2 -dimethylaminoethyl)-3-oxo-1,2,3,5-tetrahydropyrido [1,2-a)benzimidazole-4-carboxamide.

8. A compound according to claim 2 which is N-[1-(1-napthyl) ethyl[-5-(2-dimethylaminoethyl)-3-oxo-1,2,3,5-tetrahydropyrido [1,2-a]benzimidazole-4-carboxamide.

9. A compound according to claim 2 which is N-(2-chlorobenzyl)-5 -(3-dimethylaminopropyl)-3-oxo-1,2,3,5-tetrahydropyrido [1,2-a]benzimidazole-4-carboxamide.

10. A compound according to claim 2 which is N-(4-methylbenzyl)-5 -(3-dimethylaminopropyl)-3-oxo-1,2,3,5-tetrahydropyrido [1,2-a]benzimidazole-4-carboxamide.

11. A compound according to claim 2 which is N-benzyl-5-(3-dimethylaminopropyl)-3-oxo-1,2,3,5-tetrahydropyrido [1,2-a]benzimidazole-4-carboxamide.

12. A compound according to claim 2 which is N-[4-(2-ethylaminoethoxy) phenyl]-1,2-dihydro-3-hydroxy-pyrido [1,2-a ]benzimidazole-4-carboxamide.

13. A compound according to claim 1 which is N-[3-(2-diethylaminoethoxy) phenyl]-1,2-dihydro-3-hydroxy-pyrido[1,2-a ]benzimidazole-4-carboxamide.

14. A compound according to claim 1 which is N-[4-(2-cyclopropylaminoethoxy) phenyl]-1,2-dihydro-3-hydroxy-pyrido [1,2-a]benzimidazole-4-carboxamide hydrochloride.

15. A compound according to claim 1 which is N-[3-(2-isopropylaminoethoxy) phenyl]-1,2-dihydro-3-hydroxy-pyrido [1,2-a]benzimidazole-4-carboxamide.

16. A compound according to claim 1 which is N-[4-(3-butylaminopropoxy) phenyl]-1,2-dihydro-3-hydroxy-pyrido [1,2-a ]benzimidazole-4-carboxamide hydrochloride.

17. A compound according to claim 1 which is N-[3-(2-propylaminoethoxy) phenyl]-1,2-dihydro-3-hydroxy-pyrido [1,2-a ]benzimidazole-4-carboxamide.

18. A compound according to claim 1 which is N-(R)-[4-(pyrrolidinomethoxy)phenyl]-1,2-dihydro-3-hydroxy-pyrido [1,2-a]benzimidazole-4-carboxamide.

19. A compound according to claim 1 which is N-(S)-[4-(pyrrolidinomethoxy)phenyl]-1,2-dihydro-3-hydroxy-pyrido [1,2-a]benzimidazole-4-carboxamide.

20. A compound according to claim 1 which is N-[4-(2-pyrrolidinoethoxy) phenyl]-1,2-dihydro-3-hydroxy-pyrido [1,2-a ]benzimidazole-4-carboxamide.

21. A compound according to claim 1 which is N-[4-(2-diethylaminoethoxy) pyrid-3-yl]-1,2-dihydro-3-hydroxy-pyrido [1,2-a]benzimidazole-4-carboxamide.

22. A compound according to claim 1 which is N-[4-(2-pyrrolidinoethoxy) pyrid-3-yl]-1,2-dihydro-3-hydroxy-pyrido [1,2-a]benzimidazole-4-carboxamide.

23. A compound according to claim 1 which is N-[4-(2-piperidinoethoxy) pyrid-3-yl]-1,2-dihydro-3-hydroxy-pyrido [1,2-a]benzimidazole-4-carboxamide.

24. A compound according to claim 1 which is N-[4-(t-butylaminoethoxy) pyrid-3-yl]-1,2-dihydro-3-hydroxy-pyrido [1,2-a]benzimidazole-4-carboxamide.

25. A compound according to claim 1 which is N-[4-(2-ethylaminoethoxy) pyrid-3-yl]-1,2-dihydro-3-hydroxy-pyrido [1,2-a]benzimidazole-4-carboxamide.

26. A compound according to claim 1 which is N-{4-[2-(2-pyrrolidinoethoxy)ethoxy]pyrid-3-yl}-1,2-dihydro-3-hydroxy-pyrido [1,2-a]benzimidazole-4-carboxamide.

27. A compound according to claim 1 which is N-[4-(3-pyrrolidinopropoxy) pyrid-3-yl]-1,2-dihydro-3-hydroxy-pyrido [1,2-a]benzimidazole-4-carboxamide.

28. A compound according to claim 1 which N-[4-(2-ethylaminoethoxy) phenyl]5-ethyl-3-oxo-1,2,3,5-tetrahydropyrido [1,2-a]benzimidazole-4-carboxamide.

29. A compound according to claim 1 which is N-[4-(3-piperidin-1 -yl-propoxy)benzyl]5-ethyl-3-oxo-1,2,3,5-tetrahydropyrido [1,2-a]benzimidazole-4-carboxamide.

30. A compound according to claim 1 which is N-[2-fluoro-4 -(3-piperidin-1-yl-propoxy)benzyl]5-ethyl-3-oxo-1, 2,3,5-tetrahydropyrido[1,2-a]benzimidazole-4-carboxamide.

31. A compound according to claim 1 which N-[4-(3-dimethylaminopropoxy) benzyl]5-ethyl-3-oxo-1,2,3,5-tetrahydropyrido [1,2-a]benzimidazole-4-carboxamide.

32. A compound according to claim 1 which is N-[2-fluoro-4 -(2-pyrrolidin-1-yl-ethoxy)benzyl]5-ethyl-3-oxo-1, 2,3,5-tetrahydropyrido[1,2-a]benzimidazole-4-carboxamide.

33. A compound according to claim 1 which N-(R)-[4-(pyrrolidin-2 -yl-methoxy)phenyl]5-ethyl-3-oxo-1,2,3,5-tetrahydropyrido [1,2-a]benzimidazole-4-carboxamide.

34. A compound according to claim 1 which is N-(S)-[4-(pyrrolidin-2 -yl-methoxy)phenyl]5-ethyl-3-oxo-1,2,3,5-tetrahydropyrido [1,2-a]benzimidazole-4-carboxamide.

35. A compound according to claim 1 which is N-[4-(2-isopropylaminoethoxy) phenyl]5-ethyl-3-oxo-1,2,3,5-tetrahydropyrido-[1,2-a]benzimidazole-4-carboxamide.

36. A compound according to claim 1 which is N-{4-[2-(2-pyrrolidin-1-yl-ethoxy)ethoxy]phenyl}1,2-dihydro-3-hydroxy-pyrido [1,2-a]benzimidazole-4-carboxamide.

37. A compound according to claim 1 which is N-(R)-[3-fluoro-4 -(pyrrolidin-2-yl-methoxy)phenyl]1,2-dihydro-3-hydroxy-pyrido [1,2-a]benzimidazole-4-carboxamide.

38. A compound according to claim 1 which is N-(S)-[3-fluoro-4 -(pyrrolidin-2-yl-methoxy)phenyl]1,2-dihydro-3-hydroxy-pyrido [1,2-a]benzimidazole-4-carboxamide.

39. A compound according to claim 1 which is N-{4-[2-(2-morpholin-4-yl-ethoxy)ethoxy]phenyl}1,2-dihydro-3-hydroxy-pyrido [1,2-a]benzimidazole-4-carboxamide.

40. A compound according to claim 1 which is N-(4-{2-[2-(4-methylpiperazin-1-yl)ethoxy]ethoxy}phenyl)1,2-dihydro-3 -hydroxy-pyrido[1,2-a]benzimidazole-4-carboxamide.

41. A compound according to claim 1 which is N-(R)-[3-fluoro-4-(pyrrolidin-2-yl-methoxy)phenyl]5-ethyl-3-oxo-1, 2,3,5-tetrahydropyrido [1,2-a]benzimidazole-4-carboxamide.

42. A compound according to claim 1 which is N-(S)-[3-fluoro-4-(Pyrrolidin-2-yl-methoxy)phenyl]5-ethyl-3-oxo-1,2,3,5-tetrahydropyrido[1,2-a]benzimidazole-4-carboxamide.

43. A compound according to claim 1 which is N-(4-{2-[2-(4-methylpiperazin-1-yl)ethoxy]ethoxy)benzyl]1,2-dihydro-3-hydroxy-pyrido[1,2-a]benzimidazole-4-carboxamide.

44. A compound according to claim 1 which is N-{4-[2-(2-morpholin-4-yl-ethoxy)ethoxy]benzyl}1,2-dihydro-3-hydroxy-pyrido [1,2-a]benzimidazole-4-carboxamide.

45. A compound according to claim 1 which is N-(4-{2-[2-(methylamino)ethoxy]ethoxy}benzyl)1,2-dihydro-3-hydroxy-pyrido [1,2-a]benzimidazole-4-carboxamide.

46. A compound according to claim 1 which is N-(4-{2-[2-(butylamino)ethoxy]ethoxy)benzyl]1,2-dihydro-3-hydroxy-pyrido [1,2-a]benzimidazole-4-carboxamide.

47. A compound according to claim 1 which is N-(4-{2-[2-(dimethylamino)ethoxy]ethoxy)benzyl]1,2-dihydro-3-hydroxy-pyrido [1,2-a]benzimidazole-4-carboxamlde.

48. A compound according to claim 1 which is N-(2-fluoro-{4-[3-(4-methylpiperazin-1-yl)propoxy]benzyl)1,2-dihydro-3-hydroxy-pyrido [1,2-a]benzimidazole-4-carboxamide.

49. A compound according to claim 1 which is N-{4-[(propylamino)methyl]phenyl}1,2-dihydro-3-hydroxy-pyrido [1,2-a]benzimidazole-4-carboxamide.

50. A compound according to claim 1 which is N-{4-[(4-methylpiperazin-1-yl)methyl]phenyl)1,2-dihydro-3-hydroxy-pyrido [1,2-a]benzimidazole-4-carboxamide.

51. A compound according to claim 1 which is N-{4-[2-(ethylamino) ethoxy]phenyl}5-(2-ethoxyethyl)-3-oxo-1,2,3,5-tetrahydropyrido [1,2-a]benzimidazole-4-carboxamide.

52. A compound according to claim 1 which is N-[4-(pyrrolidin-1-yl-methyl)phenyl]1,2-dihydro-3-hydroxy-pyrido [1,2-a]benzimidazole-4-carboxamide.

53. A compound according to claim 1 which is N-{4-[2-(ethylamino) ethoxy}5-(2-piperidin-1-yl-ethyl)-3-oxo-1,2,3,5-tetrahydropyrido [1,2-a]benzimidazole-4-carboxamide.

54. A compound according to claim 1 which is N-[4-(2-piperidin-1-yl-ethoxy)benzyl]5-(2-ethoxyethyl)-3-oxo-1,2,3,5-tetrahydropyrido[1,2-a]benzimidazole-4-carboxamide.

55. A compound according to claim 1 which is N-[4-(2-piperidin-1-yl-ethoxy)benzyl]5-(2-ethylaminoethyl)-3-oxo-1, 2,3,5-tetrahydropyrido[1,2-a]benzimidazole-4-carboxamide.

56. A compound according to claim 1 which is N-[4-(2-piperidin-1-yl-ethoxy)benzyl]5-ethyl-3-oxo-1,2,3,5-tetrahydropyrido [1,2-a]benzimidazole-4-carboxamide.

57. A compound according to claim 1 which is N-(4-{2-[(2-morpholin-4-yl-ethyl)amino]ethoxy}benzyl)5-ethyl-3-oxo-1, 2,3,5-tetrahydropyrido[1,2-a]benzimidazole-4-carboxamide.

\* \* \* \* \*